United States Patent [19]

Murase

[11] Patent Number: 4,924,874
[45] Date of Patent: May 15, 1990

[54] AUTOMATIC BLOOD PRESSURE MEASURING APPARATUS

[75] Inventor: Tadashi Murase, Gifu, Japan

[73] Assignee: Colin Electronics Co., Ltd., Aichi, Japan

[21] Appl. No.: 317,953

[22] Filed: Mar. 2, 1989

[51] Int. Cl.$^5$ .................................. A61B 5/02
[52] U.S. Cl. ..................... 128/682; 128/681
[58] Field of Search ............ 128/672, 677–686, 128/687–688

[56] References Cited

U.S. PATENT DOCUMENTS

| | | | |
|---|---|---|---|
| 4,484,584 | 11/1984 | Uemura | 128/681 X |
| 4,729,383 | 3/1988 | Susi | 128/681 |
| 4,774,960 | 10/1988 | Arnold et al. | 128/681 |

Primary Examiner—Angela D. Sykes
Attorney, Agent, or Firm—Oliff & Berridge

[57] ABSTRACT

An apparatus for automatically measuring blood pressure of a subject based on heartbeat-synchronous pulses, the apparatus having a device including a cuff and detecting a magnitude of each of the pulses produced from the subject as pressure in the cuff is varied, a device for collecting not less than a first number of the detected pulses, and plotting a corresponding number of points in a table defined by a first axis indicative of the cuff pressure and a second axis indicative of the pulse magnitude, such that each of the plotted points represents a cuff pressure at a time of detection of a corresponding one of the collected pulses and a pulse magnitude of the corresponding one pulse, a device for selecting a second number of consecutive points from the plotted points and determining a regression line of the selected points, a device for determining, based on the regression line, at least one expected pulse magnitude regarding at least one point adjacent to the selected points, a device for determining a temporary maximum blood pressure based on the at least one point if a pulse magnitude represented by each of the at least one point is higher than a corresponding one of the at least one expected pulse magnitude, a device for determining a proper maximum blood pressure, and a device for displaying the temporary maximum blood pressure prior to the proper maximum blood pressure.

8 Claims, 3 Drawing Sheets

AUTOMATIC BLOOD PRESSURE MEASURING APPARATUS

BACKGROUND OF THE INVENTION

1. Field of the Invention

The present invention generally relates to an automatic blood pressure measuring apparatus, and particularly to such an apparatus which displays temporary maximum blood pressure before displaying proper maximum blood pressure.

2. Discussion of the Prior Art

There is known an automatic blood pressure measuring apparatus including an inflatable cuff which is set around a body member of a subject, and means for detecting magnitudes of pulses (e.g., Korotkoff sounds) produced from the body member synchronously with heartbeat of the subject at each of continuous blood pressure measuring cycles, as pressure in the cuff is varied at each measuring cycle. The apparatus automatically determines a blood pressure of the subject based on the detected variation in magnitude of the heartbeat-synchronous pulses at each measuring cycle.

In the above apparatus, maximum and/or minimum blood pressure are/is not displayed until the pressure of the cuff is decreased from an upper predetermined level to a lower predetermined level at each measuring cycle, namely, magnitude variation of heartbeat-synchronous pulses is detected at each measuring cycle. However, maximum blood pressure is clinically important information. Thus, it is desirable that maximum blood pressure be earlier displayed as temporary maximum blood pressure than proper maximum blood pressure that is determined with higher accuracy based on the magnitude variation of the pulses detected at each measuring cycle and displayed at the end of the measuring cycle.

It has been proposed the art of determining temporary maximum blood pressure, in which a maximum difference in magnitude between each pair of consecutive two pulses is determined when pulses are consecutively detected at each measuring cycle and temporary maximum blood pressure is determined based on a magnitude of the pulse corresponding to the determined maximum difference. In this case, however, the maximum difference may be changed one after another as pulses are consecutively detected, whereby the temporary maximum blood pressure once determined and displayed may be replaced with another determined based on another maximum difference.

SUMMARY OF THE INVENTION

It is therefore an object of the present invention to provide a blood pressure measuring apparatus which automatically determines a temporary maximum blood pressure with reliability.

The above object has been achieved by the present invention, which provides an apparatus for automatically measuring blood pressure of a subject based on heartbeat-synchronous pulses produced from the subject, the apparatus comprising (a) detecting means including an inflatable cuff set around a body portion of the subject, the detecting means detecting a magnitude of each of the heartbeat-synchronous pulses produced from the body portion as pressure in the inflatable cuff is varied, (b) plotting means for collecting not less than a first predetermined number of the detected pulses, and plotting a corresponding number of points in a two-dimensional table defined by a first axis indicative of the pressure of the cuff and a second axis indicative of the magnitude of the pulses, such that each of the plotted points represents a cuff pressure at a time of detection of a corresponding one of the collected pulses and a pulse magnitude of the corresponding one pulse, (c) first determining means for selecting a second predetermined number of consecutive points from the plotted points, and determining a regression line of the selected consecutive points, (d) second determining means for determining, based on the regression line, at least one expected pulse magnitude regarding at least one point adjacent to the selected consecutive points in the plotted points, (e) third determining means for determining a temporary maximum blood pressure of the subject based on the at least one point if a pulse magnitude represented by each of the at least one point is higher than a corresponding one of the at least one expected pulse magnitude, (f) fourth determining means for determining a proper maximum blood pressure of the subject, and (g) display means for displaying the temporary maximum blood pressure before displaying the proper maximum blood pressure.

In the automatic blood pressure measuring apparatus constructed as described above, not less than the first predetermined number of heartbeat-synchronous pulses are collected from the pulses detected by the detecting means, and a corresponding number of points are plotted in the pulse magnitude/cuff pressure two-dimensional table. The second predetermined number of consecutive points are selected from the plotted points and a regression line of the selected points is determined in the two-dimensional table. Further, at least one expected pulse magnitude is determined regarding at least one point adjacent to the selected consecutive points in the plotted points, based on the determined regression line. If a magnitude of each of the at least one point actually detected by the detecting means is higher than a corresponding one of the at least one expected pulse magnitude, a temporary maximum blood pressure is determined based on a cuff pressure represented by the at least one point. The thus determined temporary blood pressure is displayed, before proper (and more accurate) maximum blood pressure is determined and displayed.

Thus, in the present apparatus, temporary maximum blood pressure is earlier determined and displayed prior to proper maximum blood pressure. Furthermore, the temporary maximum blood pressure once determined and displayed is not changed since it is determined based on a heartbeat-synchronous pulse whose magnitude is higher than an expected pulse magnitude determined regarding the pulse, in contrast to the conventional apparatus of the type in which temporary maximum blood pressure is determined based on a maximum difference in magnitude between each pair of adjacent two pulses of consecutively detected pulses and may be replaced one after another as the pulses are consecutively detected. Also, for the same reason as indicated above, the temporary maximum blood pressure determined and displayed by the present apparatus is satisfactory in accuracy and therefore reliable.

In a preferred embodiment of the apparatus of the present invention, the detecting means detects the heartbeat-synchronous pulses at each of continuous blood pressure measuring cycles as the pressure of the cuff is varied at the each measuring cycle, the plotting means collecting not less than the first number of the detected pulses and plotting a corresponding number of points in the two dimensional table at the each measuring cycle, the first determining means selecting the second number of consecutive points from the plotted points and determining a regression line of the selected consecutive points at the each measuring cycle, the second determining means determining, based on the regression line, at least one expected pulse magnitude regarding at least one point adjacent to the selected consecutive points at the each measuring cycle, the third determining means determining, at the each measuring cycle, a temporary maximum blood pressure of the subject based on the at least one point if a pulse magnitude represented by each of the at least one point is higher than a corresponding one of the at least one expected pulse magnitude, the fourth determining means determining a proper maximum blood pressure of the subject at the each measuring cycle, the display means displaying at the each measuring cycle the temporary maximum blood pressure before displaying the proper maximum blood pressure. In this case, it is preferred that the continuous blood pressure measuring cycles be effected at predetermined regular time intervals.

In another embodiment of the apparatus of the invention, the heartbeat-synchronous pulses consist of Korotkoff sounds produced from the body portion of the subject synchronously with heartbeat of the subject.

In yet another embodiment of the apparatus of the invention, the detecting means detects the heartbeat-synchronous pulses as the pressure of the cuff is decreased.

According to a feature of the apparatus of the invention, the first predetermined number is five.

According to another feature of the apparatus of the invention, the second predetermined number is three.

According to yet another feature of the apparatus of the invention, the first predetermined number is five, the second predetermined number is three, the at least one point consists of a pair of points following the selected consecutive points, the at least one expected pulse magnitude consists of a pair of expected pulse magnitudes determined regarding the pair of points, and a cuff pressure represented by one of the pair of points is determined as the temporary maximum blood pressure if a pulse magnitude represented by each of the pair of points is higher than a corresponding one of the pair of expected pulse magnitudes.

BRIEF DESCRIPTION OF THE DRAWINGS

The above and optional objects, features and advantages of the present invention will be better understood by reading the following detailed description of the presently preferred embodiment of the invention, when considered in conjunction with the accompanying drawings, in which.

DETAILED DESCRIPTION OF THE PREFERRED EMBODIMENT

Figure 1:
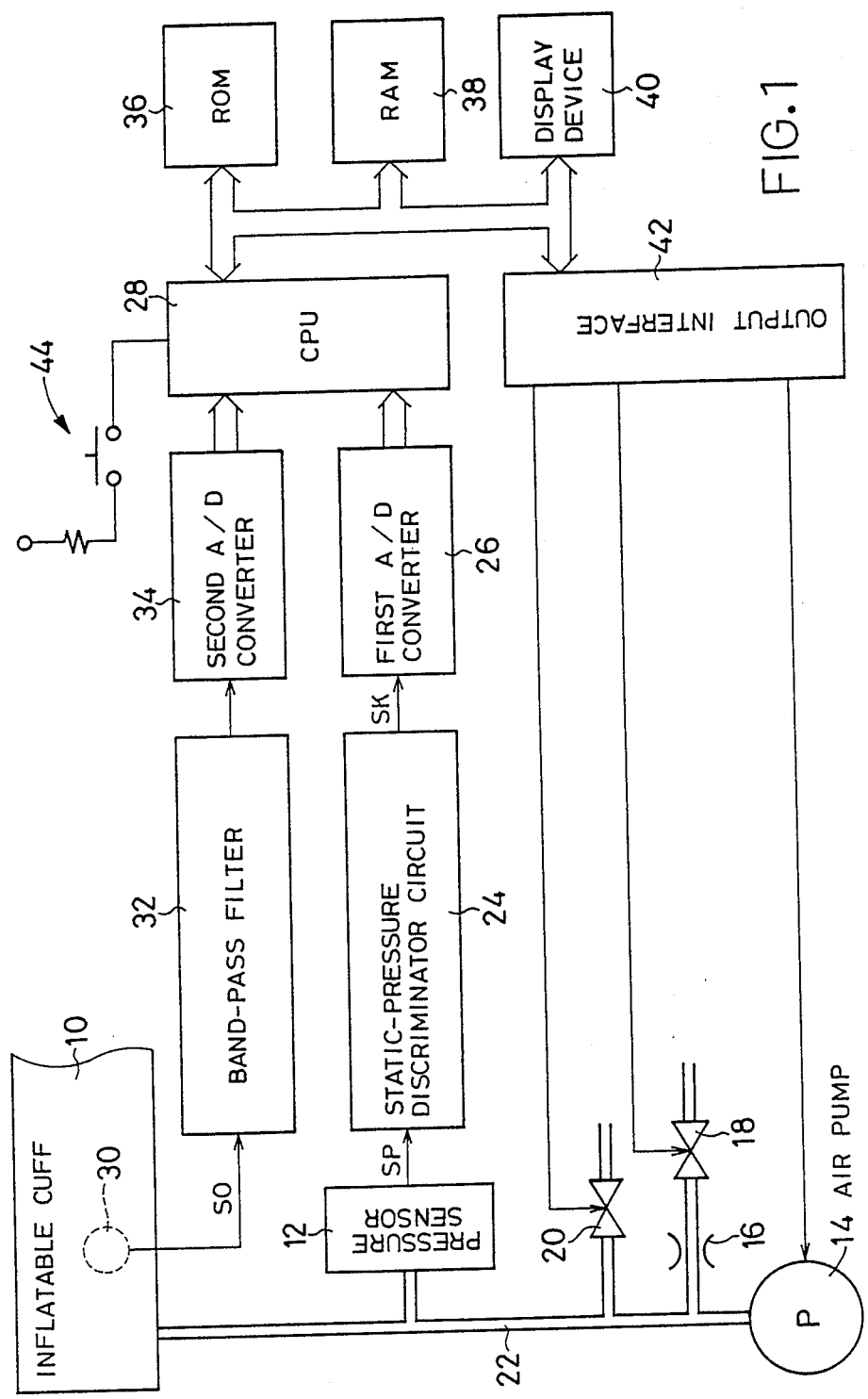
FIG. 1 is a diagrammatic view of an automatic blood pressure measuring apparatus of the present invention.

Referring first to FIG. 1, there is diagrammatically illustrated an automatic blood pressure measuring apparatus embodying the present invention. In the figure, reference numeral 10 designates an inflatable cuff which is set around an upper arm of a subject. The cuff 10 is formed of rubber and has a bag-like structure. The cuff 10 is connected via a piping 22 to a pressure sensor 12, an air pump 14, a slow-deflation restrictor 16, a slow-deflation electromagnetic valve 18 and a rapid-deflation electromagnetic valve 20. The pressure sensor 12 detects pressure in the cuff 10 and generates pressure signal SP representing the detected pressure in the cuff 10, to a static pressure discriminator circuit 24. The discriminator circuit 24 includes a low-pass filter which separates, from signal SP, signal SK representing static pressure in the cuff 10 (hereinafter, referred to as cuff pressure P), and cuff pressure signal SK is supplied to a CPU 28 via a first A/D (analog-to-digital) converter 26.

A microphone 30 is disposed in the cuff 10. The microphone 30 detects pulse sounds produced from the upper arm of the subject synchronously with heartbeat of the subject (i.e., Korotkoff sounds; hereinafter, referred to as K sounds), and generates signal SO representing the detected K sounds, to a band-pass filter 32. The band-pass filter 32 selectively transmits signal in a frequency range of 30 to 80 Hz corresponding to the frequency of K sounds. K-sound signal SO transmitted through the band-pass filter 32 is supplied to the CPU 28 via a second A/D converter 34. In the present embodiment, the K sounds correspond to heartbeat-synchronous pulses produced from the subject.

The CPU 28 is coupled via data bus to a ROM (read only memory) 36, a RAM (random access memory) 38, a display device 40 and an output interface 42, and processes the received signals according to software programs pre-stored in the ROM 36 by utilizing temporary-storage function of the RAM 38. The CPU 28 effects a series of operations for measuring blood pressure, by controlling the operation of each of the air pump 14 and pair of electromagnetic valves 18, 20. In other words, the CPU 28 automatically determines blood pressure of the subject based on K-sound signal SO and cuff-pressure signal SK, and commands the display device 40 to display the determined blood pressure.

Figure 2:
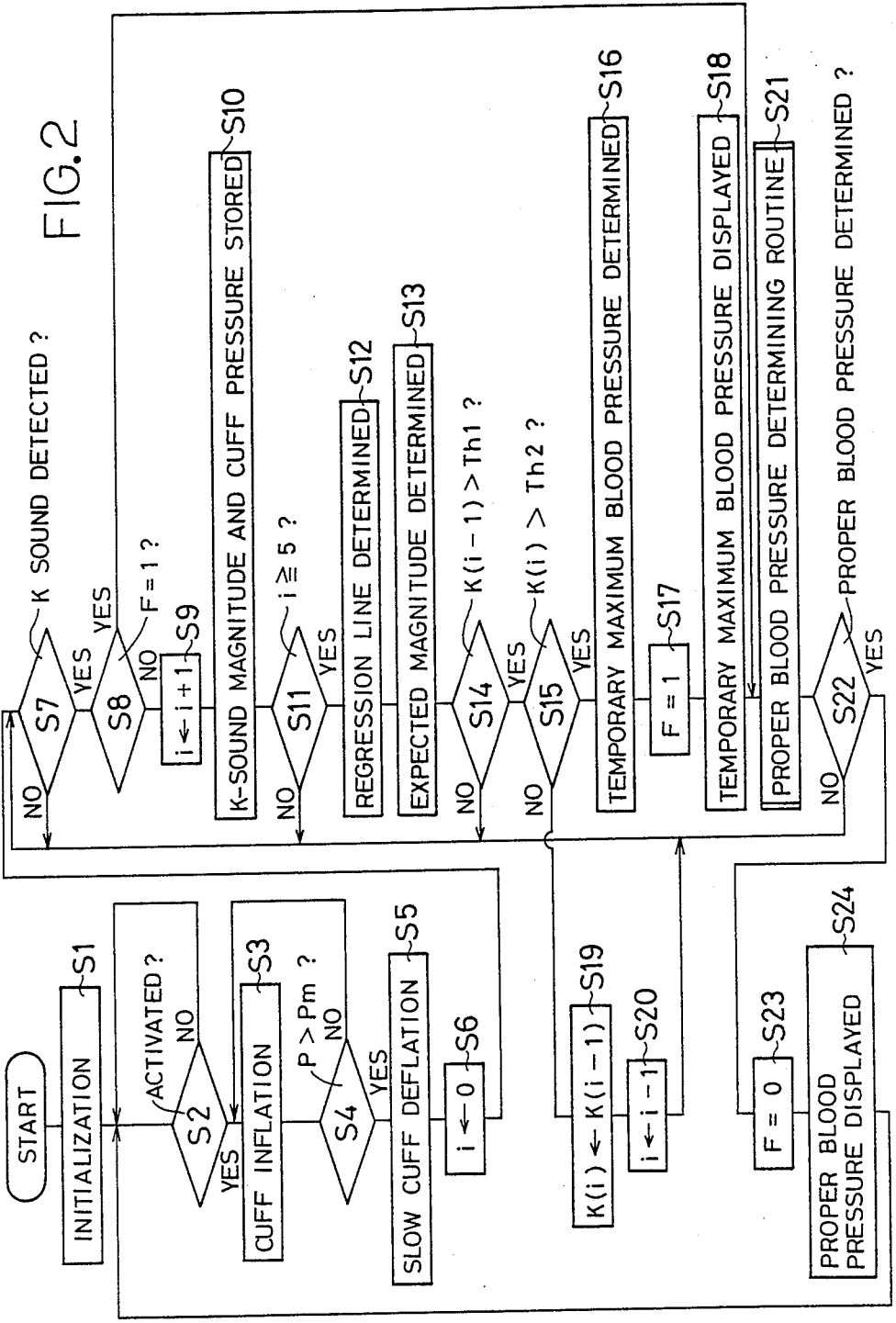
FIG. 2 is a flow chart illustrating the operation of the apparatus of FIG. 1.

Referring next to FIG. 2, there is illustrated the flow chart according to which the present blood pressure measuring apparatus is operated to automatically determine and display a temporary maximum blood pressure of the subject at a comparatively early stage in each of continuous blood pressure measuring cycles, before determining and displaying a proper maximum blood pressure of the subject at the end of each measuring cycle.

Upon application of electric power to the apparatus, the control of the CPU 28 goes to step S1 at which the initialization of the apparatus is effected. Step S1 is followed by step S2 at which it is judged whether or not a current blood pressure measuring cycle has been started as a result of operation of an activation switch 44 (FIG. 1), or as a result that a timer of an activation circuit (not shown) has counted a predetermined value corresponding to a predetermined regular time interval at which continuous blood pressure measuring cycles are effected.

If the judgement at step S2 is negative, step S2 is repeated until the judgement is turned affirmative. Meanwhile, if the judgement at step S2 is affirmative, step S2 is followed by step S3 at which the pair of valves 18, 20 are closed and the air pump 14 is activated, so as to inflate the cuff 10, namely, increase cuff pressure P. Step S3 is followed by step S4 at which it is judged whether or not cuff pressure P has been increased to an upper target pressure level Pm. Upper target level Pm is predetermined to be suffficiently higher than estimated maximum blood pressure of the subject, for example 180 mmHg. Steps S3 and S4 are repeated until cuff pressure P exceeds upper target level Pm. If the judgement at step S4 is turned affirmative, namely, if cuff pressure P has exceeded upper target level Pm, step S4 is followed by step S5 at which the air pump 14 is stopped and the slow-deflation valve 18 is opened, so as to slowly deflate the cuff 10, namely, decrease cuff pressure P at a comparatively low rate.

At the following step S6 count or content i of index counter is reset to zero. The index counter serves to give an index number to each of sets of data (described below) which represents a magnitude of a K sound and a cuff pressure at the time of detection of the K sound.

Step S6 is followed by step S7 at which it is judged whether or not a K sound has been detected, namely, whether or not K-sound signal SO representing a K sound has been supplied to the CPU 28. If the judgement at step S7 is negative, step S7 is repeated until the judgement is turned affirmative. Meanwhile, if the judgement at step S7 is affirmative, step S7 is followed by step S8 at which a magnitude of the detected K sound (given in the form of a magnitude of signal SO) together with a cuff pressure at the time of the detection of the K sound, are stored in the RAM 38. In the present embodiment, the cuff 10, microphone 30, a band-pass filter 32, step S7 stored in the form of software program in the ROM 36, the CPU 28 and RAM 38 for effecting step S7, and others serve as the means for detecting the heartbeat-synchronous pulses.

At the following step S8 it is judged whether or not flag F is placed at F=1. The affirmative judgement at step S8, namely, that flag F is at F=1, means that a temporary maximum blood pressure has been determined already at the current measuring cycle. On the other hand, the negative judgement at step S8, namely, that flag F is at F=0, means that a temporary maximum blood pressure has not been determined yet at the current measuring cycle. If the judgement at step S8 is negative, the control of the CPU 28 goes to step S9 at which content i of the index counter is incremented by one to i+1. Step S9 is followed by step S10 at which a set of data representing the magnitude of the K sound and the cuff pressure at the time of the detection of the K sound, both of which have been read in at step S7, is given an index number i by the index counter and stored in a memory region in the RAM 38 corresponding to the index number i.

Figure 3:
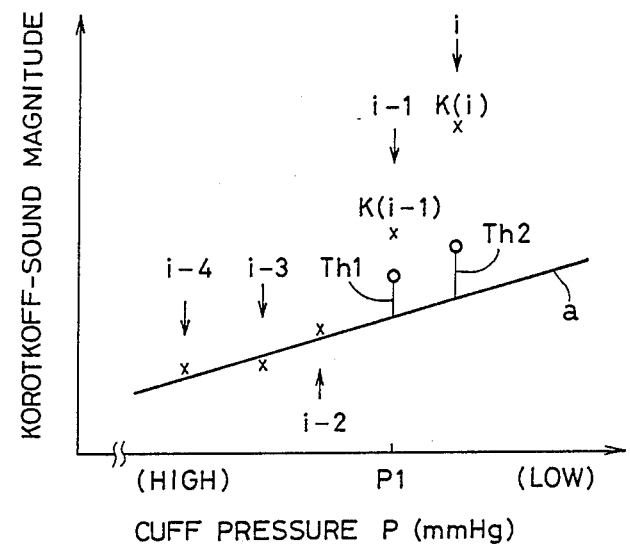
FIG. 3 is a graph showing points corresponding to Korotkoff sounds detected through a microphone of the apparatus of FIG. 1.

Step S10 is followed by step S11 at which it is judged whether or not content i of the index counter is not less than 5. If the judgement at step S11 is negative, steps S7 through S11 are repeated to detect another K sound, increment content i by one, and store a set of data representing a magnitude of the K sound and a cuff pressure at the time of detection of the K sound, in a memory region corresponding to the index number i equal to the current content i of the index counter. Based on each of sets of data stored in the corresponding memory regions, a point is plotted in a two-dimensional table defined by an axis of abscissa indicative of cuff pressure P and an axis of ordinate indicative of K-sound magnitude, as shown in FIG. 3. The plotting of the points in the table is not written on a sheet of paper or the like, but actually is effected on a calculation basis by the CPU 28. Meanwhile, if the judgement at step S11 is turned affirmative, namely, if five of K sounds have been detected and content i of the index counter has been increased to five, the control of the CPU 28 goes to step S12. In the present embodiment, steps S9 through S11 stored in the ROM 36 and the CPU 28 and RAM 38 for effecting those steps, serve as the means for collecting not less than a predetermined number of the pulses, and plotting a corresponding number of pulses in the pulse magnitude/cuff pressure two-dimensional table.

At step S12, three consecutive points are selected from the five points in the two-dimensional table and a regression line of the three consecutive points is determined. Regarding five points i-4, i-3, i-2, i-1, i in the table of FIG. 3, three consecutive points i-4, i-3 and i-2 are selected and a regression line a of the selected three points is determined.

Regression line a of three points is expressed by the following linear function, formula (1):

$$Y = p \cdot X + q \qquad (1)$$

, wherein
X: cuff pressure
Y: K-sound magnitude
p: constant (slope of line a), and
q: constant (y intercept of line a).

Constants p, q are calculated by the following formulas (2) and (3), respectively:

$$p = \frac{\Sigma(x - \bar{x})(y - \bar{y})}{\Sigma(x - \bar{x})} \qquad (2)$$

$$q = \bar{y} - p\bar{x} \qquad (3)$$

, wherein
x, y: x and y coordinates of each of the three points, and
$\bar{x}, \bar{y}$: averages of x and y coordinates of the three points.

Thus, in the present embodiment, step S12 stored in the ROM 36 and the CPU 28 and the RAM 38 for effecting step S12, serve as the means for determining a regression line of a predetermined number of consecutive points selected from the points plotted in the two-dimensional table.

Step S12 is followed by step S13 at which an expected K-sound magnitude Th1 regarding a point i-1 following the selected three consecutive points i-4, i-3, i-2 in the plotted five points, and an expected K-sound magnitude Th2 regarding a point i following point i-1, are determined based on regression line a and three consecutive points i-4, i-3, i-2, as follows:

First, a standard deviation s of three points i-4, i-3, i-2 is calculated by the following formula (4):

$$s = \sqrt{\frac{\Sigma(y - \bar{y})^2 - a \cdot \Sigma(x - \bar{x})(y - \bar{y})}{n - 2}} \qquad (4)$$

, wherein n: number of points (in the present embodiment, three).

Expected K-sound magnitude Th regarding point Pk is determined based on regression line a and standard deviation s, and expressed by the following formula (5):

$$a \cdot x_k + b + t_{\alpha/2} \cdot s \cdot \sqrt{1 + \frac{1}{n} + \frac{(x_k - x)^2}{\Sigma(x - x)^2}} \quad (5)$$

, wherein
$x_k$: x coordinate of point Pk,
t: value from t-Distribution Table, and
$\alpha$: significance level.

Regarding a predetermined number, n, of samples the value for t is determined from a t-Distribution Table (also known as Student's t Table), a standard reference found in most statistics textbooks, by finding the intersection of the row (column) representing degree of freedom (n−2) with the column (row) representing significance level ($\alpha$).

Point i-1 is plotted with a statistically high probability below expected value Th1. If significance level $\alpha$ is 0.05, point i-1 is plotted below value Th1 with a more than 95 percent probability. Similarly, point i is plotted with a statistically high probability below expected value Th2. Accordingly, if both points i-1, i are plotted beyond corresponding expected values Th1, Th2, it is statistically estimated that points i-1, i reflect a particular cause other than statistically expected dispersion or variation. Thus, points i-1, i considerably accurately correspond to maximum blood pressure of the subject, and temporary maximum blood pressure can be determined based on those points.

Thus, in the present embodiment, step S13 stored in the ROM 36 and the CPU 28 and RAM 38 for effecting step S13, serve as the means for determining at least one expected pulse magnitude regarding at least one point following the selected consecutive points, based on the regression line determined based on the selected consecutive points.

At the following step S14 it is judged whether or not a K-sound magnitude K(i-1) represented by point i-1 is higher than expected K-sound magnitude Th1. If the judgement at step S14 is negative, steps S7 through step S13 are repeated. Meanwhile, if the judgement at step S14 is affirmative, the control of the CPU 28 goes to step S15 at which it is judged whether or not a K-sound magnitude K(i) represented by point i is higher than expected K-sound magnitude Th2. If the judgement at step S15 is affirmative, the control of the CPU 28 goes to step S16 at which a cuff pressure P1 (FIG. 3) represented by point i-1 is determined as a temporary maximum blood pressure of the subject at the current measuring cycle. Step S16 is followed by step S17 at which flag F is placed at F=1, and at the following step S18 the temporary maximum blood pressure is displayed by the display device 40. In the present embodiment, steps S14 through S16 stored in the ROM 36 and the CPU 28 and RAM 38 for effecting those steps, serve as the means for determining the temporary maximum blood pressure.

On the other hand, if the judgement at step S15 is negative, the control of the CPU 28 goes to step S19 at which the set of data including K-sound magnitude K(i), which is stored at the corresponding memory region, is replaced with the set of data including magnitude K(i-1), which is stored in the corresponding memory region, and at the following step S20 content i of the index counter is deduced by one to i-1. Thus, is erased the set of data corresponding to point i whose K-sound magnitude is not higher than expected value Th2. Subsequently, steps S7 through S15 and steps S19 and S20 are repeated until the judgement at step S15 is turned affirmative.

After the temporary maximum blood pressure is displayed at step S18, is effected step S21, a proper blood pressure determining routine in which is effected one of well-known algorithms for determining maximum and minimum blood pressure based on variation in magnitude of all the Kototkoff sounds detected at the current measuring cycle, namely, while cuff pressure P is slowly decreased from upper pressure level Pm to a lower pressure level Pn which is predetermined to be sufficiently lower than estimated minimum blood pressure of the subject. For example, proper (and more accurate) maximum blood pressure is determined based on a Korotkoff sound whose magnitude is the highest in all the detected Korotkoff sounds, and corrected based on the minimum blood pressure which is determined based on a Korotkoff sound detected in the vicinity of the end of the current measuring cycle, namely, when cuff pressure P is decreased to a pressure level in the vicinity of lower pressure level Pn. Thus, the proper blood pressure determining routine is terminated.

Step 21 is followed by step S22 at which it is judged whether or not a proper blood pressure measurement has been terminated. If the judgement at step S22 is negative, the control of the CPU 28 returns to step S7 and subsequently step S8 at which the judgement is found to be affirmative since flag F is at F=1 at the current measuring cycle. Accordingly, steps S9 through S20 are skipped, and steps S7, S8, S21, S22 are repeated. Meanwhile, if the judgement at step S22 is affirmative, the control of the CPU 28 goes to step S23 at which flag F is reset to F=0. Step S23 is followed by step S24 at which the proper blood pressure is displayed on the display device 40, and the rapid-deflation valve 20 is opened to rapidly deflate the cuff 10, namely, decrease cuff pressure P at a comparatively high rate. Subsequently, the control of the CPU 28 returns to step S2 to effect a following blood pressure measuring cycle. Thus, the present apparatus determines a temporary maximum blood pressure and a proper maximum blood pressure at each of continuous measuring cycles. In the present embodiment, the cuff 10, microphone 30, band-pass filter 32 and step S21 stored in the ROM 36 and the CPU 28 and RAM 38 for effecting step S21, and others serve as the means for determining the proper maximum blood pressure, while the display device 40 and step S18 stored in the ROM 36 and the CPU 28 and RAM 38 for effecting step S18, serve as the means for displaying the temporary maximum blood pressure prior to the proper maximum blood pressure.

As is apparent from the foregoing, in the present embodiment, a temporary maximum blood pressure is determined and displayed at an early stage at each blood pressure measuring cycle before determination of a proper maximum blood pressure. Furthermore, since the temporary maximum blood pressure is determined based on the comparison result that an actually detected magnitude of a Korotkoff sound is higher than an expected K-sound magnitude determined regarding the K sound, the temporary maximum blood pressure once determined and displayed is by no means changed, in contrast to the conventional apparatus in which temporary maximum blood pressure is determined based on a maximum difference in magnitude between each pair of adjacent two K sounds of the K sounds consecutively detected at a measuring cycle, and therefore the temporary value once determined and displayed may be replaced with another. For the same reason as indicated above, the temporary maximum blood pressure determined and displayed by the present apparatus is satisfactory in accuracy and accordingly reliable.

In the present embodiment, if both K-sound magnitudes K(i-1) and K(i) are higher than expected K-sound magnitudes Th1 and Th2, respectively, cuff pressure P1 corresponding to K-sound magnitude K(i-1) is determined as a temporary maximum blood pressure of the subject. This leads to improving the accuracy or reliability of the temporary maximum blood pressure determined and displayed by the present apparatus.

For the same reason as indicated just above, it is unnecessary in the present embodiment to subject K-sound signal SO to a smoothing processing in which noise is removed from signal SO so as to smooth magnitudes of K sounds represented by signal SO. Thus, a temporary maximum blood pressure is determined and displayed more quickly as such at each measuring cycle.

As indicated above, in the present embodiment, if both actually detected K-sound magnitudes K(i-1) and K(i) are higher than corresponding expected K-sound magnitudes Th1 and Th2, cuff pressure P1 corresponding to K-sound magnitude K(i-1), which is next to the selected three consecutive points i-4, i-3, i-2, is determined as a temporary maximum blood pressure of the subject. However, it is possible that, if more than two actually detected K-sound magnitudes are higher than corresponding expected K-sound magnitudes, a cuff pressure represented by a second or a further following point other than a first point next to the selected three points, be determined as a temporary maximum blood pressure. Furthermore, it is possible to determine a temporary maximum blood pressure based an average of cuff pressures represented by points whose K-sound magnitudes are higher than corresponding expected K-sound magnitudes.

While in the illustrated embodiment Korotkoff sounds are utilized as heartbeat-synchronous pulses for measuring blood pressure of a subject, it is possible to utilize other heartbeat-synchronous pulses such as pulse wave (i.e., pressure oscillation transmitted to an inflatable cuff set around a body member of a subject as pressure in the cuff is varied), or vibration of a wall of an arterial vessel.

In the illustrated embodiment is determined a regression line of three consecutive K sounds selected from five Korotkoff sounds. However, a regression line may be determined regarding not less than three points. Accordingly, it is possible to determine a regression line of four or more K sounds.

While in the illustrated embodiment a regression line is determined in the two-dimensional table defined by the first axis indicative of K-sound magnitude and the second axis indicative of cuff pressure P, it is possible to determine a regression line in a two-dimensional table defined by a first axis of K-sound magnitude and a second axis of time, by utilizing a relationship between variation in cuff pressure P and elapse of time.

Although in the illustrated embodiment is used K-sound signal SO which has not been subjected to a smoothing processing, it is possible to determine a regression line based on K-sound signal SO which has been subjected to a smoothing processing.

While in the illustrated embodiment a proper blood pressure is determined on a real-time basis after the determination of a temporary maximum blood pressure, namely, the proper blood pressure determining routine of step S21 of FIG. 2 is effected each time a Korotkoff sound is detected after the determination of the temporary maximum blood pressure, it is possible to effect the proper blood pressure determining routine after all the Korotkoff sounds have been detected at a measuring cycle, namely, in a "batch" manner.

While the present invention has been described in its presently preferred embodiment with detailed particularities, it is to be understood that the invention may be embodied with various changes, modifications and improvements that may occur to those skilled in the art without departing from the scope and spirit of the invention defined in the appended claims.

What is claimed is:

1. An apparatus for automatically measuring a pressure of a subject based on heartbeat-synchronous pulses produced from the subject, the apparatus comprising:

detecting means including an inflatable cuff set around a body portion of the subject, said detecting means detecting a magnitude of each of the heartbeat-synchronous pulses produced from said body portion as pressure in said inflatable cuff is varied;

plotting means for collecting not less than a first predetermined number of the detected pulses, and plotting a corresponding number of points in a two-dimensional table defined by a first axis indicative of said pressure of the cuff and a second axis indicative of said magnitude of the pulses, such that each of the plotted points represents a cuff pressure at a time of detection of a corresponding one of the collected pulses and a pulse magnitude of said corresponding one pulse;

first determining means for selecting a second predetermined number of consecutive points from said plotted points, and determining a regression line of the selected consecutive points;

second determining means for determining, based on said regression line, at least one expected pulse magnitude regarding at least one point adjacent to said selected consecutive points in said plotted points;

third determining means for determining a temporary maximum blood pressure of the subject based, on said at least one point if a pulse magnitude represented by each of said at least one point is higher than a corresponding one of said at least one expected pulse magnitude;

fouth determining means for determining a proper maximum blood pressure of the subject; and display means for displaying said temporary maximum blood pressure before displaying said proper maximum blood pressure.

2. The apparatus as set forth in claim 1, wherein said detecting means detects the heartbeat-synchronous pulses at each of continuous blood pressure measuring cycles as the pressure of the cuff is varied at said each blood pressure measuring cycle, said plotting means collecting not less than the first number of the detected pulses and plotting a corresponding number of points in the two dimensional table at said each measuring cycle, said first determining means selecting the second number of consecutive points from the plotted points and determining a regression line of the selected consecutive points at said each measuring cycle, said second determining means determining, based on the regression line, at least one expected pulse magnitude regarding at least one point adjacent to the selected consecutive points at said each measuring cycle, said third determining means determining, at said each measuring cycle, a temporary maximum blood pressure of the subject based on the at least one point if a pulse magnitude represented by each of the at least one point is higher than a corresponding one of the at least one expected pulse magnitude, said fourth determining means determining a proper maximum blood pressure of the subject at said each measuring cycle, said display means displaying at said each measuring cycle the temporary maximum blood pressure before displaying the proper maximum blood pressure.

3. The apparatus as set forth in claim 2, wherein said continuous blood pressure measuring cycles are effected at predetermined regular intervals of time.

4. The apparatus as set forth in claim 1, wherein said heartbeat-synchronous pulses consist of Korotkoff sounds produced from said body portion of the subject synchronously with heartbeat of the subject.

5. The apparatus as set forth in claim 1, wherein said detecting means detects said heartbeat-synchronous pulses as said pressure of the cuff is decreased.

6. The apparatus as set forth in claim 1, wherein said first predetermined number is five.

7. The apparatus as set forth in claim 1, wherein said second predetermined number is three.

8. The apparatus as set forth in claim 1, wherein said first predetermined number is five, said second predetermined number being three, said at least one point consisting of a pair of points following said selected consecutive points, said at least one expected pulse magnitude consisting of a pair of expected pulse magnitudes determined regarding said pair of points, a cuff pressure represented by one of said pair of points being determined as said temporary maximum blood pressure if a pulse magnitude represented by each of said pair of points is higher than a corresponding one of said pair of expected pulse magnitudes.

* * * * *